(12) United States Patent
Gassmann

(10) Patent No.: US 7,846,314 B2
(45) Date of Patent: Dec. 7, 2010

(54) HANDLING A PLURALITY OF SAMPLES

(75) Inventor: Marcus Gassmann, Karlsruhe (DE)

(73) Assignee: Agilent Technologies, Inc, Santa Clara, CA (US)

( * ) Notice: Subject to any disclaimer, the term of this patent is extended or adjusted under 35 U.S.C. 154(b) by 1091 days.

(21) Appl. No.: 11/432,075

(22) Filed: May 11, 2006

(65) Prior Publication Data

US 2007/0261961 A1    Nov. 15, 2007

(51) Int. Cl.
*G01N 27/00* (2006.01)

(52) U.S. Cl. .................. 204/451; 204/601; 137/256; 137/861; 422/81

(58) Field of Classification Search ............. 204/451, 204/601; 137/827, 825, 256, 265, 255, 597, 137/861; 261/2, 3; 422/81
See application file for complete search history.

(56) References Cited

U.S. PATENT DOCUMENTS

| | | | | |
|---|---|---|---|---|
| 5,599,432 A | * | 2/1997 | Manz et al. | 204/451 |
| 5,800,690 A | | 9/1998 | Chow et al. | 204/451 |
| 5,976,336 A | * | 11/1999 | Dubrow et al. | 204/453 |
| 6,280,589 B1 | | 8/2001 | Manz et al. | 204/453 |
| 2002/0008029 A1 | * | 1/2002 | Williams et al. | 204/453 |

FOREIGN PATENT DOCUMENTS

WO    WO 02/22878 A1  *  3/2002

* cited by examiner

*Primary Examiner*—Nam X Nguyen
*Assistant Examiner*—J. Christopher Ball

(57) ABSTRACT

A method for handling samples in a microfluidic system is described. The microfluidic system includes an injection channel fluidically coupled to an injection point adapted for injecting an amount of fluid, a first sample well containing a first sample, the first sample well being fluidically coupled with the injection channel, and a second sample well containing a second sample, the second sample well being fluidically coupled with the injection channel. The method includes moving the second sample from the second sample well towards the first sample well.

22 Claims, 7 Drawing Sheets

HANDLING A PLURALITY OF SAMPLES

BACKGROUND

The present invention relates to a microfluidic system, and to a method for handling samples in a microfluidic system.

U.S. Pat. No. 5,800,690 "Variable Control of Electroosmotic and/or Electrophoretic Forces within a Fluid-Containing Structure via Electrical Forces" to C. Chow et al. relates to a microfluidic system, wherein electrical current or electrical parameters other than voltage are used to control the movement of fluids through the channels of the system. Time-multiplexed power supplies also provide further control over fluid movement by varying the voltage on an electrode connected to a fluid reservoir of the microfluidic system, by varying the duty cycle during which the voltage is applied to the electrode, or by a combination of both.

U.S. Pat. No. 6,280,589 "Method for Controlling Sample Introduction in Microcolumn Separation Techniques and Sampling Device" to A. Manz et al. relates to injecting a sample as a sample plug into a sampling device which comprises at least a channel for the electrolyte buffer and a supply and drain channel for the sample. The injection of the sample plug into the electrolyte channel is accomplished electrokinetically by applying an electric field across the supply and drain channels for a time at least long enough that the sample component having the lowest electrophoretic mobility is contained within the geometrically defined volume, such that the injected sample plug reflects the original sample composition.

SUMMARY OF THE DISCLOSED EMBODIMENTS

It is an object of the invention to provide a microfluidic system with an improved handling of samples. The object is solved by the independent claim(s). Further embodiments are shown by the dependent claim(s).

A method according to embodiments of the present invention is related to handling samples in a microfluidic system. The microfluidic system comprises an injection channel fluidically coupled to an injection point adapted for injecting an amount of fluid. The microfluidic system further comprises a first sample well containing a first sample, the first sample well being fluidically coupled with the injection channel, and a second sample well containing a second sample, the second sample well being fluidically coupled with the injection channel. The method comprises moving the second sample from the second sample well towards the first sample well.

In a microfluidic system comprising two or more sample wells, a flow path for draining off the second sample is introduced. Both the first and the second sample well are fluidically connected to the injection channel, and hence, there exists a junction where the first sample well is fluidically coupled with the second sample well. The second sample, which is initially contained in the second sample well, is moved from the second sample well towards the injection channel and towards the first sample well.

The proposed flow path might e.g. be advantageous in case one wants to start moving the second sample towards the injection point, though for some reason, the second sample should not be supplied to the injection point yet. As long as the second sample should not be supplied to the injection point, the second sample is moved towards the first sample well.

As soon as the second sample may be supplied to the injection point, the second sample can be provided to the injection point with small time delay. The second sample has already been moved to the junction where the first sample well is fluidically coupled with the second sample well. Hence, the second sample just has to be moved from the junction to the injection point. It is not necessary to move the second sample all the distance from the first sample well to the injection point. Accordingly, the second sample may be injected a short time after the first sample has been injected. Thus, the throughput of the microfluidic system is increased.

Using the method according to embodiments of the present invention, the microfluidic system can handle a plurality of two or more samples in a time-efficient manner. As long as the second sample should not be supplied to the injection point yet, it is moved towards the first sample well. As soon as it may be injected, the second sample is supplied to the injection point with little time delay. While supplying the second sample to the injection point, a third sample may e.g. be moved towards the first and/or the second sample well before the third sample is supplied to the injection point.

In prior art solutions, the second sample has been drained off via a side channel to an auxiliary well. In the side channel, a highly resistive depletion region has been formed, and the voltage drop across the depletion region has been likely to cause problems. For example, the voltage drop might lead to an uncontrollable current flow within the microfluidic system and thus to chip failure. Though the microfluidic system according to embodiments of the present invention might still comprise a side channel with an auxiliary well, which might e.g. be used for supplying a reference sample to the system, the second sample is moved towards the first sample well instead of being conveyed towards the side channel.

According to a preferred embodiment, the first sample has already been conveyed to the injection point at an earlier point of time. Hence, the second sample may be moved towards the first sample well and may even mix with the first sample contained in the first sample well, because the first sample is not needed any more, as it has already been supplied to the injection point at an earlier point of time. According to this embodiment, sample wells of samples that have already been processed may be used as waste wells for a second sample.

According to another preferred embodiment, the second sample may be directed towards the injection point by modifying the second sample's movement. As soon as the second sample may be injected, it is no longer drained off towards the first sample well, but is supplied to the injection point.

According to a preferred embodiment, the second sample is electrokinetically moved from the second sample well towards the first sample well. For this purpose, a suitable set of voltages and/or currents may be applied to the microfluidic system.

In a preferred embodiment, the various different samples that are moved through the microfluidic system may be electrically contacted by means of one or more electrodes. The electrodes might be positioned in one or more of the sample wells, or in close proximity to one or more of the sample wells. Further alternatively, the electrodes might be positioned in a respective channel that is in fluid communication with a respective sample well.

According to a preferred embodiment, an electric current is supplied to the first sample well. Furthermore, at the second sample well, an electric current is withdrawn. Thus, negatively charged sample compounds of the second sample are electrokinetically moved from the second sample well towards the first sample well.

According to a preferred embodiment, a set of voltages and/or currents is applied to the microfluidic system in a way that the second sample is conveyed from the second sample well to the first sample well. Then, the set of voltages and/or currents is modified such that the second sample is no longer moved to the second sample well. Instead, the second sample is redirected towards the injection channel and the injection point.

In a further preferred embodiment, when applying a first set of voltages and/or currents to the microfluidic system, the second sample is electrokinetically moved towards the first sample well, and when applying a second set of voltages and/or currents to the microfluidic system, the second sample is moved towards the injection channel and the injection point. Thus, the second sample can be redirected towards the injection point by modifying the set of voltages and/or currents applied to the microfluidic system. For example, by switching the set of voltages and/or currents, the sample might be supplied to a separation system as soon as the separation system is available.

A microfluidic system according to embodiments of the present invention comprises an injection channel fluidically coupled to an injection point adapted for injecting an amount of fluid, a first sample well containing a first sample, the first sample well being fluidically coupled with the injection channel, and a second sample well containing a second sample, the second sample well being fluidically coupled with the injection channel. The microfluidic system further comprises a control unit adapted for controlling the sample wells in order to move the second sample towards the first sample well.

According to a preferred embodiment, the microfluidic system comprises, in addition to the first and the second sample well, further sample wells containing further samples, the further sample wells being fluidically coupled with the injection channel. Thus, the microfluidic system may handle a plurality of different samples.

According to a further preferred embodiment, the second sample may be moved towards the first sample well and towards one or more of the further sample wells. By moving a sample towards two or more target sample wells, the magnitude of currents applied to each target sample well can be reduced.

In a further preferred embodiment, the microfluidic system comprises a separation system adapted for separating compounds of a sample, with the sample being supplied to the separation system via the injection channel. By integrating a separation system on a microfluidic device, the tasks of consecutively separating and analyzing a number of different samples, which might e.g. include a reference sample and unknown samples, may be performed on one single microfluidic device.

In a preferred embodiment, the separation system utilizes at least one of electrophoresis and electrochromatography for separating compounds of a sample. For example, according to a preferred embodiment, the separation system might comprise a gel-filled separation channel adapted for electrophoretically separating the sample's compounds according to their respective mobilities. The separation channel's outlet might be fluidically coupled to a detection unit, in order to detect the various compounds as a function of time.

According to a preferred embodiment, the injection channel is at least partly filled with gel, whereas at least one of the first and the second sample well is not filled with gel, but with some kind of buffer solution. When a sample passes the fluid-gel-boundary, an effect called "stacking" is observed: the velocity of the sample's compounds is slowed down, and the concentrations of the sample's various compounds in the channel are increased. This leads to a higher concentration of sample compounds in the channel relative to the well. This effect is highly appreciated, because it allows improving the signal-to-noise ratio of acquired detection signals.

According to a further preferred embodiment, the microfluidic system further comprises an auxiliary well, with the auxiliary well being fluidically coupled, via a side channel, to the injection channel. For example, the first sample may be conveyed towards the side channel before being supplied to the injection point. However, according to embodiments of the present invention, the other samples are not moved towards the auxiliary well, but towards sample wells containing samples that are not needed any more. Hence, problems related to formation of a highly resistive depletion region in the side channel will not become significant.

According to a further preferred embodiment, a reference sample is supplied to the system via the auxiliary well. Via the side channel, the reference sample may be moved to the injection point. In a preferred embodiment, a ladder sample is supplied via the auxiliary well to the separation system, in order to calibrate the separation system. The positions of peaks related to the ladder sample's various compounds are known and can be used for calibrating the separation system.

According to a preferred embodiment, the microfluidic system is made of one of: fused silica, crystalline quartz, fused quartz, plastics, silicon. According to a further preferred embodiment, the microfluidic system is microstructured using one or more of the following techniques: photolithography, wet etching, hot embossing, micromolding.

Embodiments of the invention can be partly or entirely embodied or supported by one or more suitable software programs, which can be stored on or otherwise provided by any kind of data carrier, and which might be executed in or by any suitable data processing unit. Software programs or routines are preferably applied for controlling voltages and/or currents provided to the microfluidic system.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

DETAILED DESCRIPTION OF THE DISCLOSED EMBODIMENTS

Figure 1:
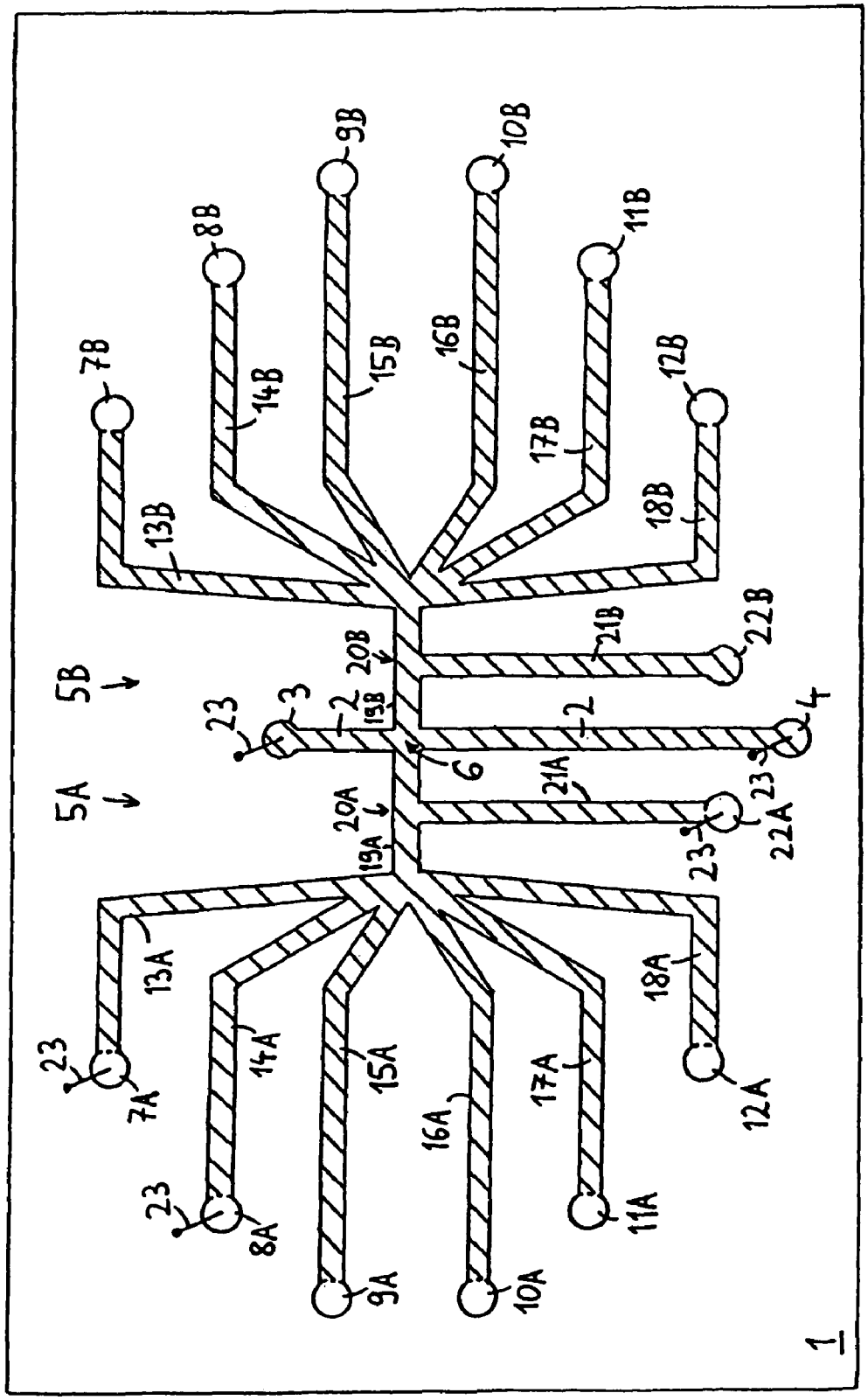
FIG. 1 shows a microfluidic device comprising a separation system.

FIG. 1 shows a microfluidic device 1 that is adapted for electrophoretically separating compounds of a sample. For this purpose, the microfluidic chip 1 comprises a separation channel 2 with an upper well 3 and a lower well 4. An injection system 5A on the left side of the microfluidic chip is adapted for injecting precisely sized analyte plugs at an injection point 6. The microfluidic device might further comprise a second injection system 5B located on the microfluidic chip's right side, which is also capable of supplying well-defined analyte plugs. The left-hand side injection system 5A comprises six sample wells 7A to 12A that are fluidically connected, via corresponding channels 13A to 18A, with an injection channel 19A. At an intersection 20A, the injection channel 19A is in fluid communication with a side channel 21A, and with an auxiliary well 22A. The intersection 20A is located at a short distance from the injection point 6. For example, the distance between the intersection 20A and the injection point 6 might be in the range of 0.1 to 2 mm, whereas the length of the injection channel 19A might be in the order of 12 mm.

The right-hand side injection system 5B comprises the same structural elements as the left-hand side injection system 5A. In FIG. 1, the structural elements of the right-hand side injection system 5B have been denoted with reference signs 7B to 22B, respectively.

For manufacturing the microfluidic device 1 shown in FIG. 1, one of the following materials may be used: fused silica, crystalline quartz, fused quartz, plastics, silicon. The wells and channels of the structure shown in FIG. 1 may be micromachined into the substrate using photolithographic procedures followed by some kind of wet etching.

Parts of the general structure shown in FIG. 1 are filled with gel, e.g. with an acrylamide gel. In FIG. 1, the gel-filled parts of the channel system have been indicated with hatching. The electrophoretic separation channel, together with its upper well 3 and its lower well 4 is filled with gel. Furthermore, the channels 13A to 18A, 13B to 18B, the injection channels 19A, 19B and the side channels 21A, 21B are filled with gel. The sample wells 7A to 12A, 7B to 12B are not filled with gel, but contain some kind of buffer solution. The auxiliary well 22B of the right-hand side injection system 5B is filled with gel, whereas the auxiliary well 22A of the left-hand side injection system 5A does not contain any gel, but is filled with buffer solution.

In order to electrokinetically move samples and their compounds through the channel system, voltages and/or currents may be applied to the wells of the microfluidic chip 1. For this purpose, wire electrodes 23 may be placed in at least some of the wells. Preferably, platinum wire electrodes are employed.

Figure 2:
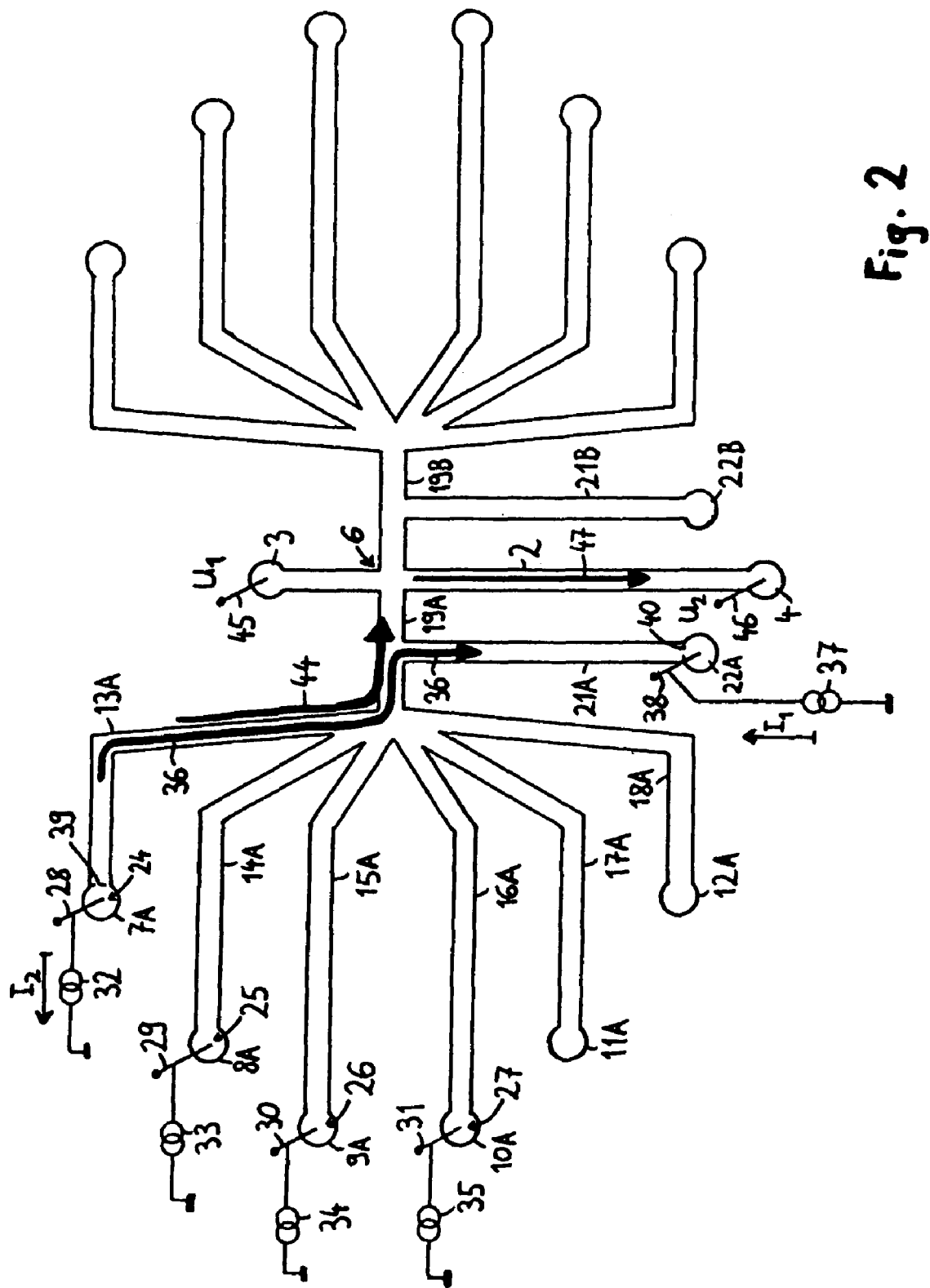
FIG. 2 depicts various different flow paths on the microfluidic device.

In FIG. 2, it is shown how the microfluidic chip of FIG. 1 can be used for electrophoretically separating compounds of a given sample. In FIG. 2, structural elements corresponding to those shown in FIG. 1 are denoted with the same reference signs as used in FIG. 1.

First of all, for calibrating the separation system, a reference sample might be analysed, with the reference sample containing a set of well-known moieties. The reference sample might either be supplied to the auxiliary well 22A or to one of the sample wells 7A to 12A. After the separation system has been calibrated, one or more unknown samples may be analyzed. For example, unknown samples 24 to 27 may be contained in respective sample wells 7A, 8A, 9A, 10A, as indicated in FIG. 2. The samples might e.g. comprise a variety of different biochemical compounds, like e.g. negatively charged DNA or RNA fragments. The samples may be electrokinetically moved within the microfluidic setup. For this purpose, the sample wells are equipped with wire electrodes. For example, the sample wells 7A, 8A, 9A, 10A are equipped with wire electrodes 28 to 31, with the wire electrodes 28 to 31 being connected to corresponding current sources 32 to 35 operating against ground.

As long as the separation channel 2 is not available yet, sample 24 may be moved towards the side channel 21A, as indicated by arrow 36. For this purpose, current source 37 supplies a current $I_1$ to a wire electrode 38 positioned in the auxiliary well 22A, and current source 32 withdraws a current $I_2$ of equal magnitude at the wire electrode 28. Preferably, the magnitude of the currents $I_1$, $I_2$ is in the order of several microampere. Thus, sample 24, which is assumed to be negatively charged, is slowly conveyed through the channel 13A, the injection channel 19A, and the side channel 21A. When the sample 24 passes the fluid-gel-boundary 39 of the sample well 7A, an effect called stacking occurs, and the sample's concentration is increased.

In the following, the effect called "stacking" will be described with regard to FIG. 3. Stacking occurs whenever a fluid containing concentrations of various different moieties passes a fluid-gel boundary. For example, in the embodiment shown in FIGS. 1 and 2, stacking occurs both at fluid-gel-boundaries of the sample wells 7A to 12A, 7B to 12B and at the fluid-gel-boundary 40 of the auxiliary well 22A.

Figure 3:
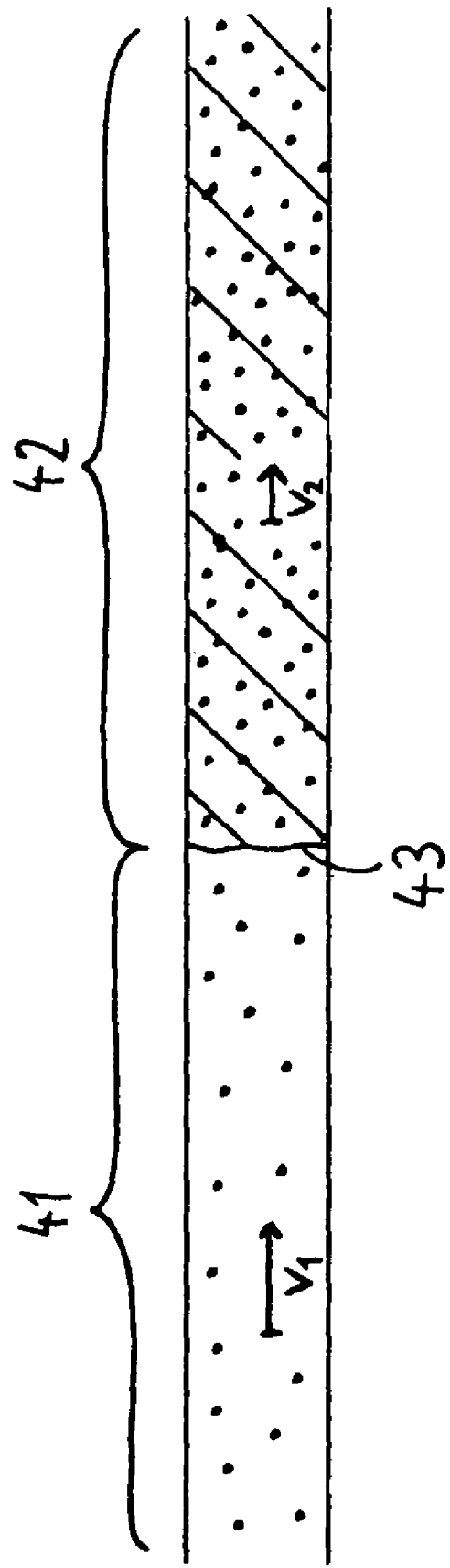
FIG. 3 illustrates an effect called "stacking"

FIG. 3 shows a portion 41 of a respective well filled with aqueous solution, and a portion 42 of a respective channel that is filled with gel. The two different media are separated by a phase boundary 43. In the portion 41, the sample's compounds move with a velocity $v_1$. When passing the phase boundary 43 between portion 41 and portion 42 and entering the gel phase, the velocity of the sample's compounds is reduced. In the gel phase, the sample's compounds move with a velocity $v_2$. As a consequence, in portion 42, the concentration of sample compounds is increased. This effect, which will further on be referred to as "stacking", is appreciated, because it gives rise to an improved signal-to-noise ratio of acquired detection signals.

As soon as the separation channel 2 becomes available, voltages and/or currents applied to the various electrodes are switched in a way that the movement of sample 24 is redirected towards the injection point 6, as indicated by arrow 44. By switching from the flow path indicated by arrow 36 to the flow path indicated by arrow 44, the sample 24 can be provided to the injection point 6 with low delay, with the delay being mainly determined by the distance between the intersection 20A and the injection point 6.

When the sample reaches the injection point 6, a sample plug of well-defined size is injected to the separation channel 2. Voltages $U_1$, $U_2$ are applied to the wire electrodes 45, 46 of the upper and the lower well 3, 4, in order to electrophoretically separate the compounds of sample 24. After traversing the separation channel 2 in the direction indicated by arrow 47, the various compounds arrive successively at the lower well 4, which is fluidically coupled to a detection unit. There, peaks related to the various moieties contained in sample 24 may be recorded as a function of time.

In prior art solutions, sample 25 is conveyed towards side channel 21A and auxiliary well 22A while the separation of sample 24 is still running. Sample 25 is conveyed towards side channel 21A while sample 24 is being analysed, in order to reduce the delay between analysis of sample 24 and injection of sample 25.

Figure 4:
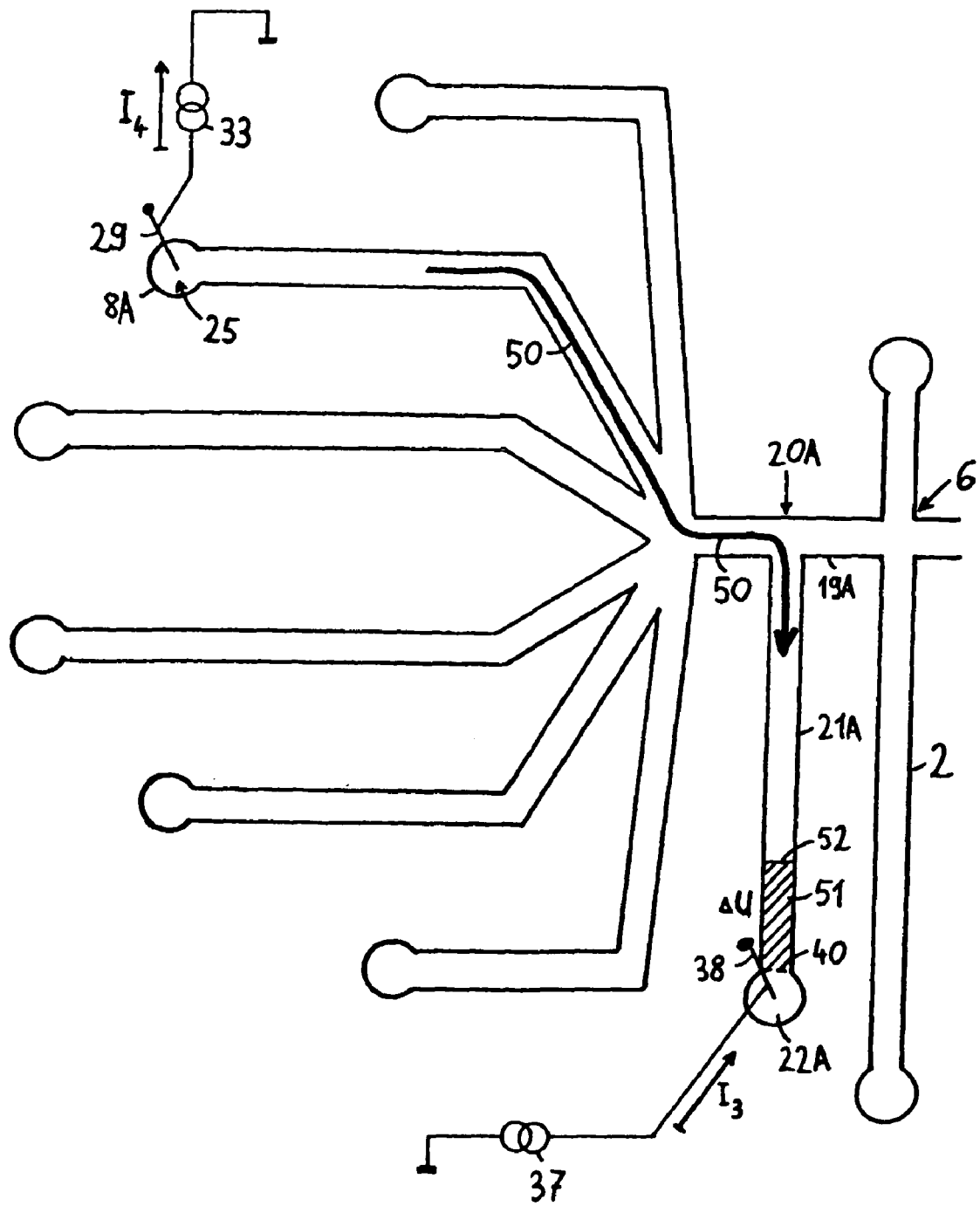
FIG. 4 shows the formation of a highly resistive depletion layer.

FIG. 4 illustrates a prior art solution of this type. For electrokinetically moving the sample 25 in the direction indicated by arrow 50, a current $I_3$ is supplied to the wire electrode 38, and a current $I_4$ of equal magnitude is withdrawn at the wire electrode 29. However, moving samples from the sample wells 7A to 12A towards the side channel 21A and the auxiliary well 22A may cause a number of problems. As a consequence of applying the currents $I_3$, $I_4$, a highly resistive depletion region 51 is formed starting at the fluid-gel-boundary 40. As long as the currents $I_3$, $I_4$ are applied, the size of the depletion region 51 will grow, with the depletion region's front 52 slowly moving upwards. The formation of the depletion region 51 can be understood as follows: at the lower end of the side channel 21A, small anions like e.g. $Cl^-$, which are highly mobile, tend to quickly move towards the positively charged auxiliary well 22A. However, only a few positively charged cations, like e.g. Na$^+$, migrate from the auxiliary well 22A into the gel-filled side channel 21A. As a result, the concentration of charged ions in the lower part of the side channel 21A decreases, and a steadily growing depletion region 51 is formed. In the article "Formation of a Resistive Region at the Anode End in DNA Capillary Electrophoresis" by Olga Bilenko at al., Electrophoresis, 24, 7-8 (April, 2003), pp. 1176-1183, the formation of the resistive depletion region is described in more detail.

The decreased concentration of charged ions in the depletion region 51 gives rise to an increased resistance of the depletion region 51, and hence, the voltage drop ΔU across the depletion region 51 is increased as well. In order to supply the predefined currents $I_3$, $I_4$ to the wire electrodes 38 and 29, the current sources have to increase the voltages supplied to the wire electrodes 38 and 29, which might lead to problems. For example, the voltage drop ΔU might lead to an uncontrollable current flow within the microfluidic system and thus to chip failure. In the course of the measurements, the size of the depletion region 51 increases continuously, and hence, also the voltage drop ΔU across the depletion region 51 steadily increases, which makes the problem even worse. Another point is that if the depletion region's front 52 gets close to the intersection 20A, it will start to disturb the movement of the sample in the injection channel 19A. Therefore, as soon as the depletion region's front 52 reaches the intersection 20A, the electrophoretic separation devices must not be used anymore.

Figure 5A:
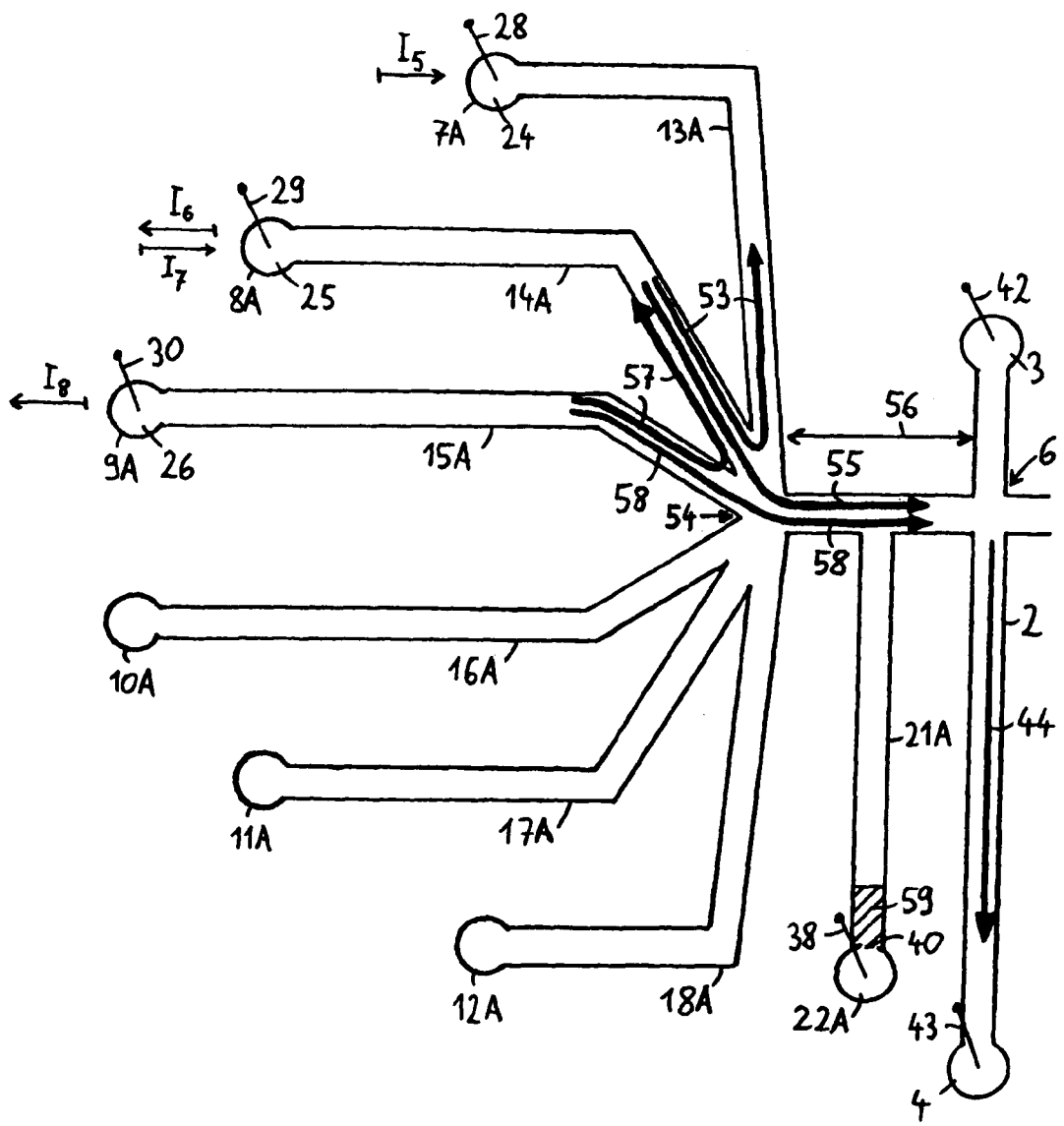
FIGS. 5a and 5b show a variety of different flow paths according to embodiments of the present invention.

FIG. 5A shows an embodiment of the present invention that attempts to overcome the problems caused by the highly resistive depletion region. In this embodiment, the sample 25 contained in sample well 8A is no longer moved towards the side channel 21A and the auxiliary well 22A while the separation channel 2 is busy. Instead, as long as the separation channel 2 is occupied, the sample 25 is electrokinetically moved via the channels 14A and 13A to the sample well 7A. This movement is indicated by arrow 53. Sample well 7A, which contains sample 24, may be used as a waste well, because sample 24 has already been supplied to the injection point 6 at an earlier point of time. For conveying sample 25 from sample well 8A to sample well 7A, a current $I_5$ is supplied at sample well 7A, and a current $I_6$ is withdrawn at sample well 8A.

As indicated by arrow 53, sample 25 is moved via channel 14A to junction 54, and via channel 13A towards the sample well 7A. When the separation channel 2 becomes available, the set of currents and/or voltages applied to the system's wire electrodes is switched in a way that sample 25 is electrokinetically moved towards the injection point 6, as indicated by arrow 55. Sample 25 is already present at the junction 54, and therefore, sample 25 only has to traverse the distance 56 before being supplied to the injection point 6. Hence, the time delay between availability of the separation channel 2 and injection of the sample 25 is kept quite small.

While the compounds of sample 25 are being separated, as indicated by arrow 44, sample 26 contained in sample well 9A is electrokinetically moved towards sample well 8A, as indicated by arrow 57. This might e.g. be done by supplying a current $I_7$ to a wire electrode 29, and by withdrawing a current $I_8$ of equal magnitude at a wire electrode 30. As soon as the compounds of sample 25 have been separated, sample 26 is supplied to the separation system. For this purpose, the currents and/or voltages applied to the respective wire electrodes are modified such that sample 26 is supplied to the injection point 6, as indicated by arrow 58. Then, sample 26 is injected into the separation system. The time delay between availability of the separation system and injection of sample 26 is determined by the time required for traversing the distance 56.

In the embodiment shown in FIG. 5A, a growth of the depletion region 59 is observed whenever a current is applied to auxiliary well 22A. However, only sample 24 is drawn towards the side channel 21A, whereas the other samples 25, 26, etc. are not drawn towards the side channel 21A. Hence, only the movement of the first sample 24 contributes to the propagation of depletion region 59 in the side channel 21A, whereas the movements of the other samples 25, 26 etc. do not contribute to the growth of depletion region 59.

Compared to prior art solutions, the propagation of the depletion region is significantly reduced. As a consequence, it takes much longer until the depletion region's front reaches the injection channel and starts disturbing the analysis. For this reason, lifetime of the microfluidic system is increased. A large number of measurements may be performed before the microfluidic system has to be replaced by a new microfluidic system. By reducing the size of the depletion region, the depletion region's total resistance is reduced, and the voltage drop across the depletion region is decreased. As a consequence, disturbances of the applied voltages and/or currents related to this voltage drop are reduced.

Figure 5B:
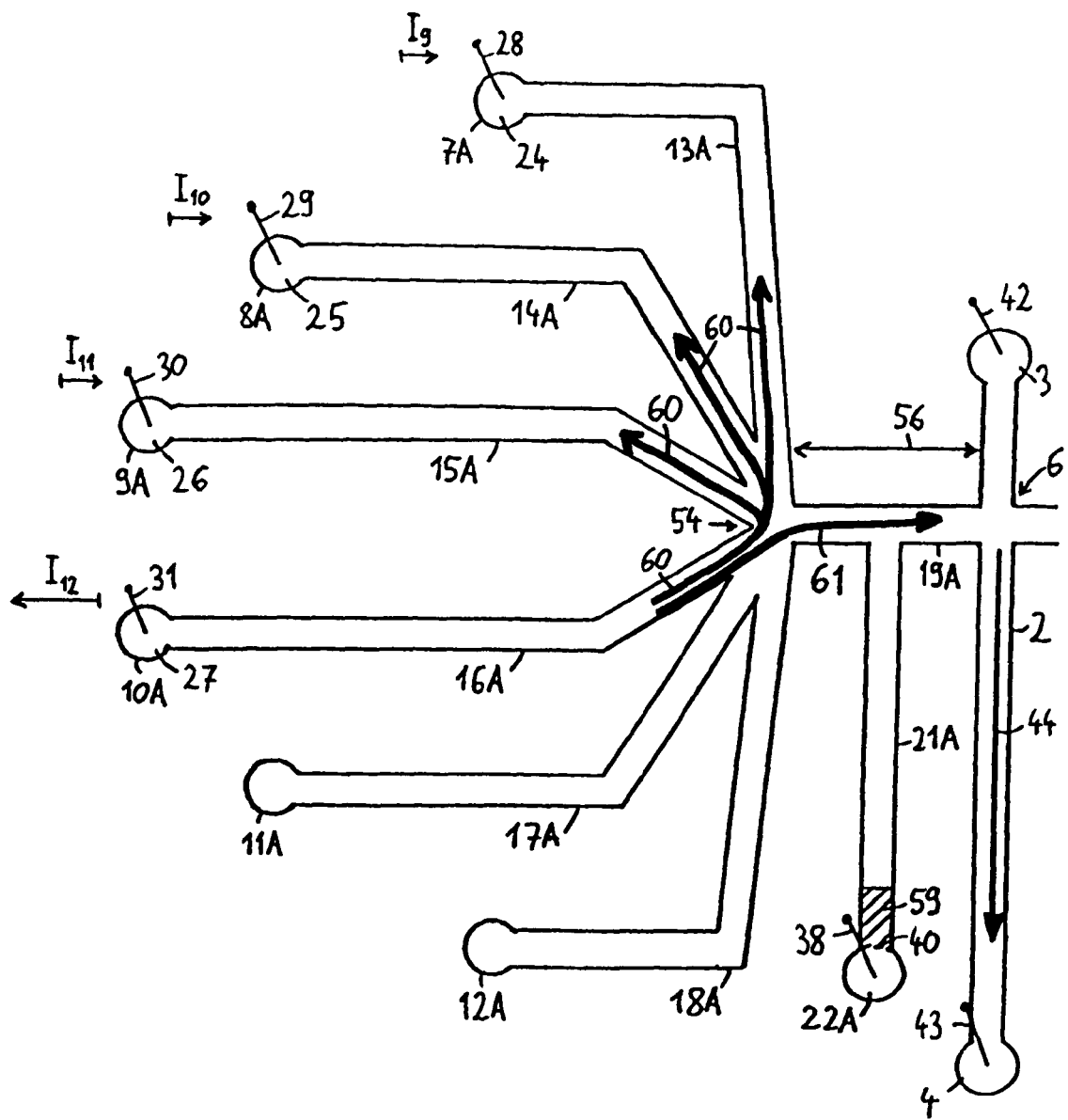

FIG. 5B shows an alternative embodiment of the present invention, whereby features that are substantially or functionally equal or similar to the features shown in FIG. 5A will be referred to by the same reference signs. In the embodiment of FIG. 5B, sample 27 contained in sample well 10A is electrokinetically moved via junction 54 towards the three sample wells 7A, 8A and 9A. The movement of sample 27 is indicated by arrow 60. Currents $I_9$, $I_{10}$, and $I_{11}$ are applied to sample wells 7A, 8A and 9A, respectively, and at sample well 10A, a current $I_{12}$ is withdrawn. The sum of the magnitudes of $I_9$, $I_{10}$, and $I_{11}$ is equal to the magnitude of $I_{12}$. As soon as the separation system becomes available, the set of currents and/or voltages is switched such that sample 27 is supplied to the injection point 6, as indicated by arrow 61.

In the embodiment of FIG. 5B, the average magnitude of the currents supplied to the sample wells is smaller than in the embodiment shown in FIG. 5A, because the current is distributed to several sample wells.

Figure 6:
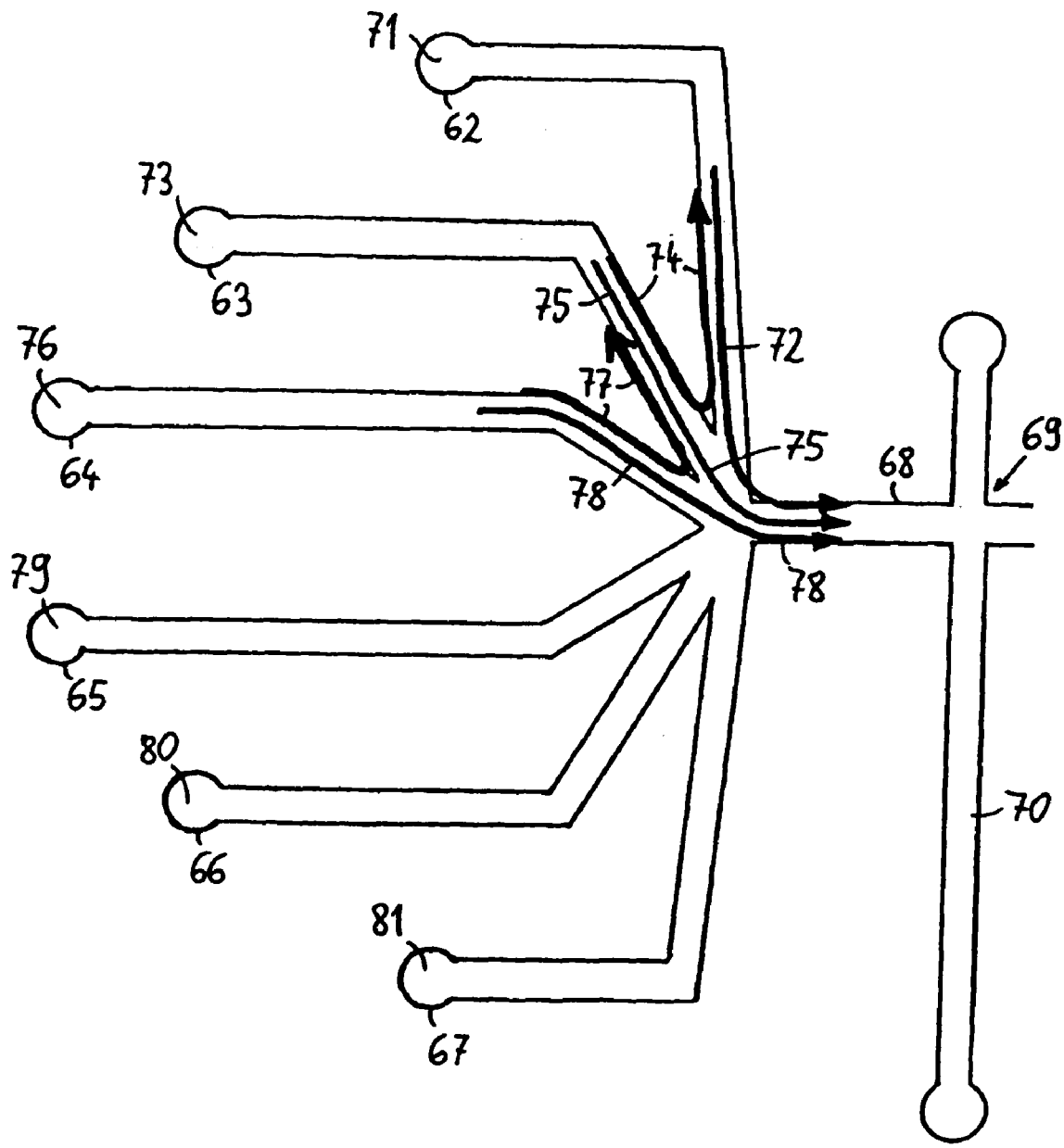
FIG. 6 shows an alternative embodiment of the invention.

FIG. 6 shows an alternative embodiment of the invention. In this embodiment, six sample wells 62 to 67 are fluidically coupled via an injection channel 68 with an injection point 69. Via the injection point 69, a sample may be supplied to a separation channel 70. In contrast to the embodiments that have previously been described, the embodiment of FIG. 6 does not comprise any side channel or auxiliary well. In the course of operation, a sample 71 contained in sample well 62 is supplied to the injection point 69, as indicated by arrow 72. During the separation of the compounds of sample 71, sample 73 is moved towards sample well 62, as indicated by arrow 74. When the separation of sample 71 is finished, the currents and/or voltages applied to the system are modified such that sample 73 is conveyed towards injection point 69, as indicated by arrow 75. Sample 73 is injected into the separation system. While the separation is carried out, a sample 76 contained in sample well 64 is electrokinetically moved towards sample well 63. Arrow 77 corresponds to this movement of sample 76. As soon as the separation system is available, sample 76 may be supplied to the injection point 69, as indicated by arrow 78. Then, samples 79, 80, 81 may be processed in a similar manner.

What is claimed is:

1. A method for handling samples in a microfluidic system, the microfluidic system comprising:
   an injection channel fluidically coupled to an injection point adapted for injecting an amount of fluid;
   a first sample well containing a first sample to be analyzed by a first separation, the first sample well being fluidically coupled with the injection channel, via a first sample channel
   a second sample well containing a second sample to be analyzed by a second separation, the second sample well being fluidically coupled with the injection channel; via a second sample channel
   the method comprising:
   moving the first sample to the injection point;
   analyzing the first sample; and
   moving the second sample from the second sample well towards the first sample well such that the second sample enters the first sample channel before moving the second sample to the injection point for analysis.

2. The method of claim 1, comprising
   supplying the second sample to the injection point by modifying the movement of the second sample and moving the second sample via the injection channel to the injection point.

3. The method of claim 1, wherein the second sample is electrokinetically moved from the second sample well towards the first sample well.

4. The method of claim 1, comprising
   applying at least one of voltages and currents to the second sample well and to the first sample well, in order to electrokinetically move the second sample towards the first sample well.

5. The method of claim 1, comprising
   supplying a current to the first sample well, and withdrawing a current at the second sample well.

6. The method of claim 1, comprising
   modifying a set of voltages and/or currents applied to electrodes of the microfluidic system to stop movement of the second sample towards the first sample well upon reaching the injection point.

7. The method of claim 1, wherein the microfluidic system comprises further sample wells containing further samples, the further sample wells being fluidically coupled with the injection channel;
   and wherein the method comprises
   moving the second sample from the second sample well towards the first sample well and one or more of the further sample wells.

8. The method of claim 1, with the microfluidic system further comprising a separation system adapted for separating compounds of the first and second samples received via the injection point.

9. The method of claim 1, with the microfluidic system further comprising a side channel fluidically coupled to the injection channel at an intersection point located between the sample wells and the injection point, the side channel being fluidically coupled with an auxiliary well.

10. The method of claim 9, comprising
    moving the second sample from the second sample well towards the auxiliary well and the first sample well.

11. The method of claim 9, comprising
    applying at least one of voltages and currents to the second sample well, to the auxiliary sample well and to the first sample well, in order to electrokinetically move the second sample towards the auxiliary sample well and the first sample well.

12. The method of claim 9, comprising
    supplying a reference sample adapted for calibrating a separation system to the auxiliary well,
    moving the reference sample from the auxiliary well via the side channel and the injection channel to the injection point, and injecting an amount of reference sample to the separation system.

13. The method of claim 9, wherein
    the side channel is at least partly filled with a first substance and the auxiliary well is at least partly filled with a second substance, and the microfluidic system includes at least one of the following features:
    the first substance is a gel;
    the second substance is a buffer solution.

14. A microfluidic system comprising
    an injection channel fluidically coupled to an injection point adapted for injecting an amount of fluid;
    a first sample well containing a first sample to be analyzed by a first separation, the first sample well being fluidically coupled with the injection channel; via first sample channel
    a second sample well containing a second sample to be analyzed by a second separation, the second sample well being fluidically coupled with the injection channel;
    a control unit configured for controlling the sample wells to move the first sample to the injection point, performing an analysis of the first sample, and moving the second sample towards the first sample well such that the second sample enters the first sample channel before moving the second sample to the injection point for analysis.

15. The microfluidic system of claim 14, further comprising a power supply adapted for supplying at least one of voltages and currents to the second sample well and to the first sample well, in order to electrokinetically move the second sample towards the first sample well.

16. The microfluidic system of claim 15, wherein the power supply is adapted for supplying a current to the first sample well, and for withdrawing a current at the second sample well.

17. The microfluidic system of claim 14, further comprising further sample wells containing further samples, the further sample wells being fluidically coupled with the injection channel.

18. The microfluidic system of claim 14, wherein
    the injection channel is at least partly filled with a first substance and the sample wells are at least partly filled with a second substance, and the microfluidic system includes at least one of the following features:
    the first substance is a gel;
    the second substance is a buffer solution.

19. The microfluidic system of claim 14, further comprising at least one of the following features:
    a separation system adapted for separating compounds of the first and second samples;
    the separation system comprises a separation column;
    the separation system comprises a detection unit, with the separation column's outlet being fluidically coupled with the detection unit;

the separation system is adapted for separating compounds of the first and second sample using one of the following separation techniques: electrophoresis, electrochromatography.

20. The microfluidic system of claim 14, further comprising a side channel fluidically coupled to the injection channel at an intersection point located between the sample wells and the injection point, the side channel being fluidically coupled with an auxiliary well.

21. The microfluidic system of claim 14, with the microfluidic system being made of at least one of: fused silica, crystalline quartz, fused quartz, plastics, silicon.

22. The microfluidic system of claim 14, with the microfluidic system being microstructured using one or more of the following techniques: photolithography, wet etching, hot embossing, micromolding.

* * * * *

UNITED STATES PATENT AND TRADEMARK OFFICE
CERTIFICATE OF CORRECTION

| | |
|---|---|
| PATENT NO. | : 7,846,314 B2 |
| APPLICATION NO. | : 11/432075 |
| DATED | : December 7, 2010 |
| INVENTOR(S) | : Marcus Gassmann |

It is certified that error appears in the above-identified patent and that said Letters Patent is hereby corrected as shown below:

In column 9, lines 8-9, in Claim 1, delete "channel, via a first sample channel" and insert -- channel via a first sample channel; --, therefor.

In column 9, lines 12-13, in Claim 1, delete "channel; via a second sample channel" and insert -- channel via a second sample channel; --, therefor.

In column 10, lines 25-26, in Claim 14, delete "channel; via first sample channel" and insert -- channel via a first sample channel; --, therefor.

Signed and Sealed this
First Day of March, 2011

David J. Kappos
*Director of the United States Patent and Trademark Office*